(12) United States Patent
Fabritius et al.

(10) Patent No.: US 12,281,343 B2
(45) Date of Patent: Apr. 22, 2025

(54) BIOTECHNOLOGICAL PRODUCTION OF DIOLS

(71) Applicant: SYMRISE AG, Holzminden (DE)

(72) Inventors: Dirk Fabritius, Ansbach (DE); Stefan Lambrecht, Hehlen (DE); Johannes Panten, Höxter (DE); Marcus Eh, Holzminden (DE)

(73) Assignee: SYMRISE AG, Holzminden (DE)

( * ) Notice: Subject to any disclaimer, the term of this patent is extended or adjusted under 35 U.S.C. 154(b) by 563 days.

(21) Appl. No.: 17/625,395

(22) PCT Filed: Jul. 8, 2019

(86) PCT No.: PCT/EP2019/068224
§ 371 (c)(1),
(2) Date: Jan. 7, 2022

(87) PCT Pub. No.: WO2021/004614
PCT Pub. Date: Jan. 14, 2021

(65) Prior Publication Data
US 2023/0212616 A1   Jul. 6, 2023

(51) Int. Cl.
*C12N 9/04* (2006.01)
*C12P 7/02* (2006.01)
*C12P 7/26* (2006.01)

(52) U.S. Cl.
CPC .............. *C12P 7/02* (2013.01); *C12N 9/0006* (2013.01); *C12P 7/26* (2013.01); *C12Y 101/0105* (2013.01)

(58) Field of Classification Search
None
See application file for complete search history.

(56) References Cited

U.S. PATENT DOCUMENTS 5,892,062 A   4/1999 Pickenhagen

FOREIGN PATENT DOCUMENTS

WO   2014209230 A1   12/2014

OTHER PUBLICATIONS

Mampel et al. (Arch. Microbiol 183: pp. 130-139, 2005).*
Liu et al. (Uniprot Accession No. AOA096H8U5, Dec. 2018).*
Wang et al. (Biotechnology & Biotechnological Equipment, vol. 33, No. 1, pp. 268-277, 2019).*
Ngo et al. in The Protein Folding Problem and Tertiary Structure Prediction, 1994, Merz et al. (ed.), Birkhauser, Boston, MA, pp. 433 and 492-495.*
International Search Report and Written Opinion in PCT/EP2019/068224. Mailed Apr. 9, 2020. 16 pages.
Muser, Edmund et al. "Functional Expression, Purification, and Characterization of 3[alpha]-Hydroxysteroid Dehydrogenase/Carbonyl recution from Comamonas testeroni". Biochemical and Biophysical Research , No., Communications, vol. Jun. 2000.
Abraham, Wolf-Rainer et al. "Abstract" Zeitschrift Fuer Naturforschung. C, A Journal of Biosciences. vol. 42, No. 4, Apr. 1, 1987.

* cited by examiner

*Primary Examiner* — Richard G Hutson
(74) *Attorney, Agent, or Firm* — Meunier Carlin & Curfman LLC

(57) ABSTRACT

The present invention relates to a method for the stereo selective production of a trans-diol or a cis-diol or a hydroxyketone comprising the step(s) (i) conversion of a trans-diol or a cis-diol to a hydroxyketone and/or (ii) conversion of a hydroxyketoneto a cis-diol or a trans-diol, catalyzed by an enzyme, which is encoded by a nucleic acid sequence of SEQ ID NO: or wherein the enzyme comprises an amino acid sequence of SEQ ID NO: 2. The present invention also relates to the use of an enzyme encoded by a nucleic acid sequence of SEQ ID NO: 1 or wherein the enzyme comprises an amino acid sequence of SEQ ID NO: 2 for the conversion of a trans-diol to a cis-diol or for the conversion of a trans-diol or a cis-diol to a hydroxy ketone and/or the conversion of a hydroxyketone to a trans-diol or a cis-diol.

6 Claims, No Drawings

Specification includes a Sequence Listing.

BIOTECHNOLOGICAL PRODUCTION OF DIOLS

CROSS-REFERENCE TO RELATED APPLICATIONS

This application is a national stage application filed under 35 U.S.C. § 371 of PCT/EP2019/068224 filed Jul. 8, 2019, which is fully incorporated by reference and made a part hereof.

REFERENCE TO AN ELECTRONIC SEQUENCE LISTING

The content of the electronic sequence listing submitted on Oct. 7, 2022, as a text file named "SM6128-02WO_ST25," created on Sep. 22, 2022, and having a size of 7,547 bytes, is herein incorporated by reference in its entirety pursuant to 37 C.F.R. § 1.52 (e) (5).

The present invention relates to a method for the stereo selective production of a trans-diol or a cis-diol or a hydroxyketone comprising the step(s) (i) conversion of a trans-diol or a cis-diol to a hydroxyketone and/or (ii) conversion of a hydroxyketone, optionally the hydroxyketone obtained in step (i), to a cis-diol or a trans-diol, wherein the conversion(s) is/are catalyzed by an enzyme, which is encoded by a nucleic acid sequence of SEQ ID NO: 1 or wherein the enzyme comprises an amino acid sequence of SEQ ID NO: 2. In particular, the present invention provides a method for the conversion of a trans-diol to a cis-diol, preferably the conversion of trans-cedrene diol to cis-cedrene diol. The present invention also relates to the use of an enzyme, which is encoded by a nucleic acid sequence of SEQ ID NO: 1 or wherein the enzyme comprises an amino acid sequence of SEQ ID NO: 2 for the conversion of a trans-diol to a cis-diol or for the conversion of a trans-diol or a cis-diol to a hydroxyketone and/or the conversion of a hydroxyketone to a trans-diol or a cis-diol, preferably for the conversion of trans-cedrene diol to cis-cedrene diol.

Cedrene diols are important starting materials for the synthesis of high quality fragrances. For example, EP0857723A1 describes the synthesis of enantiopure Ambrocenide.

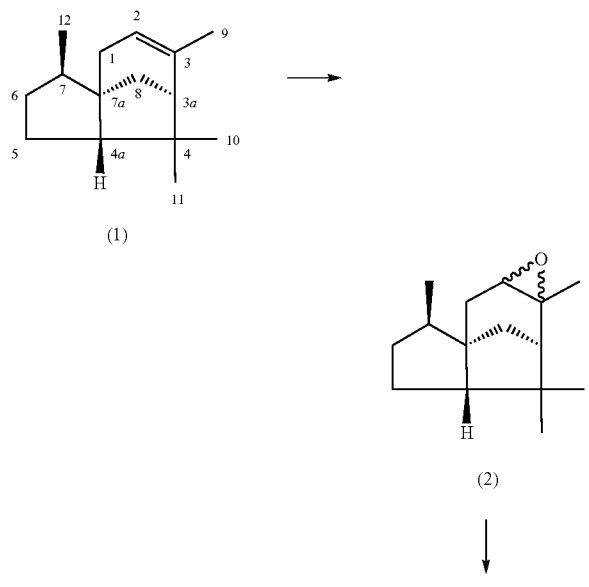

Scheme 1: Synthesis of Cedrene diol according to EP0857723

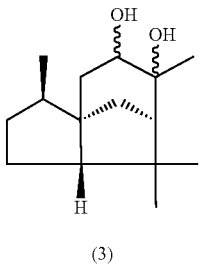

Due to its exceptional fragrance properties as acetonide, cis-(8R,9S)-cedrende diol is of particular interest. Starting from a-cedrene, cedrene expoxide is produced by chemical epoxidation. Subsequently, the epoxide is opened hydrolytically with acid catalysis to a mixture of trans- and cis-cedrene diols. In this process, the desired (8R,9S)-cis-cedrene diol is only obtained in small amounts and has to be laboriously purified. Therefore, the proposed chemical synthesis is very difficult and only provides the desired product in low yield after extensive physical purification. Consequently, it is necessary to develop new strategies for the synthesis of the desired (8S,9R)-cis-cedrene diol, which allow to obtain the product in high purity and high yield.

As substrate for the biotechnological synthesis of the desired (8R,9S)-cis-cedrene diol, only 8R-cedrol, α-cedrene and (-)-α-cedrene epoxide are commercially available. Starting from α-cedrene, up to now, there are only chemical cis-dihydroxylations known, which require the use of very toxic substances such as osmium tetroxide. Enzymatic dihydroxylations by dioxygenases are so far only described for aromatic systems (Faber, K. (1995): Biotransformations in organic chemistry. Springer Verlag Berlin Heidelberg New York; Nolan, L. C.; O'Connor, K. E. (2008): Dioxygenase- and monooxygenase-catalysed synthesis of cis-dihydrodiols, catechols, epoxides and other oxygenated products. Biotechnol. Lett., 30, 1879-1891). For the opening of an epoxide to a cis-diol, there are no suitable epoxide hydrolases described in the prior art. A 9-hydroxylation of (8R)-cedrol would always yield a different epimer (8S,9R) than the desired (8R,9S)-cis-cedrene diol. (8S)-cedrol is not commercially available. In the prior art, there are different microbial biotransformations of (8R)-cedrol and α-cedrene described. Abraham et al. describe a 9-hydroxylation of (8R)-cedrol by a fungus, which yields a (8S,9S)-trans-cedrene diol (Abraham, W. A.; Washausen, P.; Kieslich, K. (1987): Microbial hydroxylation of cedrol and cedrene. Z. Naturforsch., 42c, 414-419). Collins et al. describe the synthesis of a different cis-cedrene diol by fungi of genus curvularia. However, this product is allegedly a (7,8)-cis-cedrene diol (Collins, D. O.; Reese, P. B. (2001): Biotransformation of cedrol by curvularia lunata ATCC®12017™ (Curvularia pseudobrachyspora Marin et al.), Phytochemistry, 56, 417-421). Consequently, the prior art does not provide a biotechnological method for producing the desired (8R,9S)-cis cedrene diol.

If cedrene expoide is to be used as substrate for the synthesis, in a first reaction, trans-cedrene diol has to be produced by an epoxide hydrolase.

Scheme 2: Opening of cedrene epoxide to give (8R,9R)-trans-cedrene diol by limonene-1,2-epoxide hydrolase.

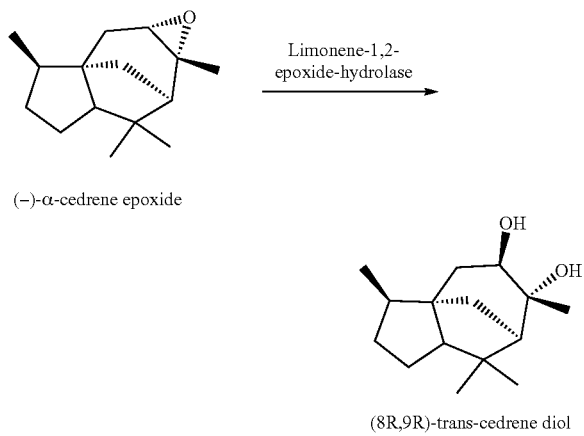

(−)-α-cedrene epoxide (8R,9R)-trans-cedrene diol

During preliminary work in the context of the present invention, a suitable epoxide hydrolase from *Rhodococcus erythropolis* DCL14 could be identified for the hydrolytic opening of the epoxide. The limonene-1,2-epoxide hydrolase was purified and characterized by van der Werf, and the gen was sequenced (Van der Werf, M. J.; Overkamp, K. M.; de Bont, J. A. M. (1998): Limonen-1,1-epoxide from *Rhodococcus erythropolis* DCL14 belongs to a novel class of epoxide hydrolases. J. of Bac., 180 (19), 5052-5057; Van der Werf, M. J.; Orru, R. V. A.; Overkamp, K. M.; Swarts, H. J.; Osprian, I.; Steinreiber, A.; de Bont, J. A. M.; Faber, K. (1999): Substrate specifity and stereospecifity of limonene-1,2-epoxide hydrolase from *Rhodococcus erythropolis* DCL14; an enzyme showing sequential and enantioconvergent substrate conversion. Appl. Microbiol. Biotech., 52, 380-385). The expoide hydrolase opens the cedrene epoxide exclusively to the desired (8R,9R)-trans-cedrene diol.

It was an objective of the present invention, to provide a method for the stereo selective conversion of a trans-diol to a cis-diol, in particular for the conversion of the now available (8R,9R)-trans-cedrene diol to the desired cis-(8R, 9S) cedrene diol.

It was a further objective of the present invention to identify enzymes, which are capable of efficiently catalyzing the conversion of a trans-diol to a cis-diol as described above and provide the desired product in high purity and high yield.

In the context of the present invention, it was found out that by oxidation of a diol to a hydroxyketone by a dehydrogenase and a stereo selective reduction of the hydroxyketone by a dehydrogenase, the equilibrium could be shifted to yield the desired product in good yield. Advantageously, the same dehydrogenase can be used for both, the oxidation and the reduction step.

The above mentioned objectives are therefore met by a method for the production of a trans-diol or a cis-diol or a hydroxyketone comprising the step(s)

(i) conversion of a trans-diol or a cis-diol to a hydroxyketone catalyzed by an enzyme, which is encoded by a nucleic acid sequence of SEQ ID NO: 1 or a nucleic acid sequence having at least 80%, at least 85%, at least 90%, at least 91%, at least 92%, at least 93%, at least 94%, at least 95%, at least 96%, at least 97%, at least 98% or at least 99% sequence identity to SEQ ID NO: 1, or wherein the enzyme comprises an amino acid sequence of SEQ ID NO: 2 or an amino acid sequence having at least 80%, at least 85%, at least 90%, at least 91%, at least 92%, at least 93%, at least 94%, at least 95%, at least 96%, at least 97%, at least 98% or at least 99% sequence identity to SEQ ID NO: 2, and/or (ii) conversion of a hydroxyketone, optionally the hydroxyketone obtained in step (i), to a cis-diol or a trans-diol catalyzed by an enzyme as defined in step (i).

In the context of the present invention, a trans-diol and a cis-diol are vicinal diols, i.e. diols, wherein the two hydroxyl groups are attached to two adjacent carbon atoms.

Sequence identity in the context of the present invention is determined with respect to the full length of the sequence specified by a SEQ ID NO. Whenever the present disclosure relates to the percentage of identity of nucleic acid or amino acid sequences to each other these values define those values as obtained by using the EMBOSS Water Pairwise Sequence Alignments (nucleotide) program (www.ebi.ac.uk/Tools/psa/emboss_water/nucleotide.html) nucleic acids or the EMBOSS Water Pairwise Sequence Alignments (protein) program (www.ebi.ac.uk/Tools/psa/emboss_water/) for amino acid sequences. Alignments or sequence comparisons as used herein refer to an alignment over the whole length of two sequences compared to each other. Those tools provided by the European Molecular Biology Laboratory (EMBL) European Bioinformatics Institute (EBI) for local sequence alignments use a modified Smith-Waterman algorithm (see www.ebi.ac.uk/Tools/psa/and Smith, T. F. & Waterman, M. S. "Identification of common molecular subsequences" Journal of Molecular Biology, 1981 147 (1): 195-197). When conducting an alignment, the default parameters defined by the EMBL-EBI are used. Those parameters are (i) for amino acid sequences: Matrix=BLOSUM62, gap open penalty=10 and gap extend penalty=0.5 or (ii) for nucleic acid sequences: Matrix=DNAfull, gap open penalty=10 and gap extend penalty=0.5. The skilled person is well aware of the fact that, for example, a sequence encoding a protein can be "codon-optimized" if the respective sequence is to be used in another organism in comparison to the original organism a molecule originates from.

In a preferred embodiment, the method described above is for the production of a cis-diol comprising the step(s)

(i) conversion of a trans-diol to a hydroxyketone catalyzed by an enzyme, which is encoded by a nucleic acid sequence of SEQ ID NO: 1 or a nucleic acid sequence having at least 80%, at least 85%, at least 90%, at least 91%, at least 92%, at least 93%, at least 94%, at least 95%, at least 96%, at least 97%, at least 98% or at least 99% sequence identity to SEQ ID NO: 1, or wherein the enzyme comprises an amino acid sequence of SEQ ID NO: 2 or an amino acid sequence having at least 80%, at least 85%, at least 90%, at least 91%, at least 92%, at least 93%, at least 94%, at least 95%, at least 96%, at least 97%, at least 98% or at least 99% sequence identity to SEQ ID NO: 2, and (ii) conversion of a hydroxyketone, optionally the hydroxyketone obtained in step (i), to a cis-diol catalyzed by an enzyme as defined in step (i).

The enzyme used in step (i) and/or step (ii) is a 3-alpha-hydroxysteroid dehydrogenase or reductase from Comamonas *testosteroni*, which shows surprisingly good results. The 3-alpha-hydroxysteroid dehydrogenase is encoded by a nucleic acid sequence according to SEQ ID NO: 1. The translated amino acid sequence of the enzyme is represented by the sequence of SEQ ID NO: 2.

Preferably, in the method described above, the two hydroxyl groups of the trans-diol and/or the cis-diol is/are attached to an aliphatic ring system comprising 2 to 4 bridged or non-bridged rings. In this context "attached to an aliphatic ring system" means that the hydroxyl groups occupy two adjacent (vicinal) positions of a ring in the ring system. In particular, the two hydroxyl groups of the trans-diol and/or the cis-diol is/are attached to a steroid compound.

In a preferred embodiment the trans-diol or the cis-diol of step (i) is obtained by a ring opening reaction from an epoxide.

In a preferred embodiment of the method described above, the trans-diol is (8R,9R)-trans-cedrene diol, the cis-diol is (8R,9S)-cis-cedrene diol and the hydroxyketone is cedrene hydroxyketone.

In one embodiment, the (8R,9S)-cis-cedrene diol or (8R,9R)-trans-cedrene diol of step (i) is obtained by a ring opening reaction from cedrene epoxide, preferably the ring opening reaction is catalyzed by an enzyme which is encoded by a nucleic acid sequence of SEQ ID NO: 3 or a nucleic acid sequence having at least 80%, at least 85%, at least 90%, at least 91%, at least 92%, at least 93%, at least 94%, at least 95%, at least 96%, at least 97%, at least 98% or at least 99% sequence identity to SEQ ID NO: 3, or wherein the enzyme comprises an amino acid sequence of SEQ ID NO: 4 or an amino acid sequence having at least 80%, at least 85%, at least 90%, at least 91%, at least 92%, at least 93%, at least 94%, at least 95%, at least 96%, at least 97%, at least 98% or at least 99% sequence identity to SEQ ID NO: 4.

The enzyme encoded by a nucleic acid sequence of SEQ ID NO: 3 or comprising an amino acid sequence of SEQ ID NO: 4 corresponds to limonene-1,2-epoxide hydrolase from the *Rhodococcus erythropolis* strain DCL14, which was found to be suitable enzyme for the ring opening reaction.

Particularly preferred is a method as described above for the production of (8R,9S)-cis-cedrene diol, wherein in step (i) (8R,9R)-trans-cedrene diol is converted to cedrene hydroxyketone and in step (ii) cedrene hydroxyketone is converted to (8R,9S)-cis-cedrene diol.

Scheme 3: Conversion (8R, 9S)-cis-cedrene diol by two dehydrogenase reactions

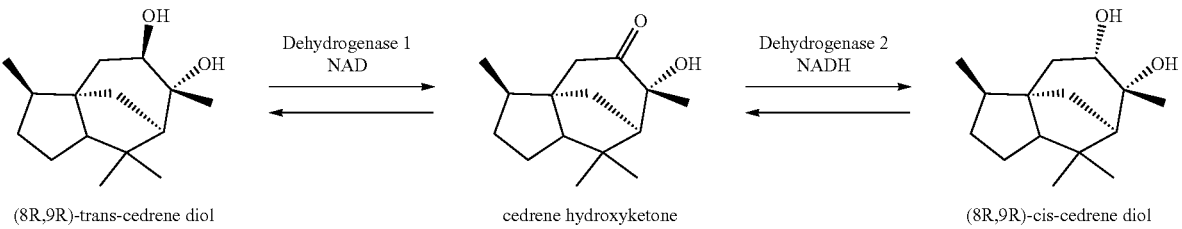

To shift the equilibrium reaction to the product side in order to obtain an efficient conversion, an excess of substrate or the cofactor is needed. Dehydrogenases usually require nicotinamide adenine dinucleotide (NAD) as cofactor for the redox reaction, which can be present in reduced form (NADH) or in oxidized form (NAD). A further variant is the phosphorylated form of NAD/NADH, i.e. NADP/NADPH. Cofactors like NAD and NADH are expensive and are therefore not used in stoichiometric amounts with respect to the substrate. In order to provide sufficient cofactor for the enzyme and thus shift the equilibrium to the product side, usually regeneration systems are used (enzyme coupled cofactor regeneration). One of the most common regeneration systems for NADH/NADPH is the use of glucose dehydrogenase as shown in Scheme 4.

Scheme 4: Stereo selective reduction of cedrene hydroxyketone with NADH regen-eration by glucose dehydrogenase

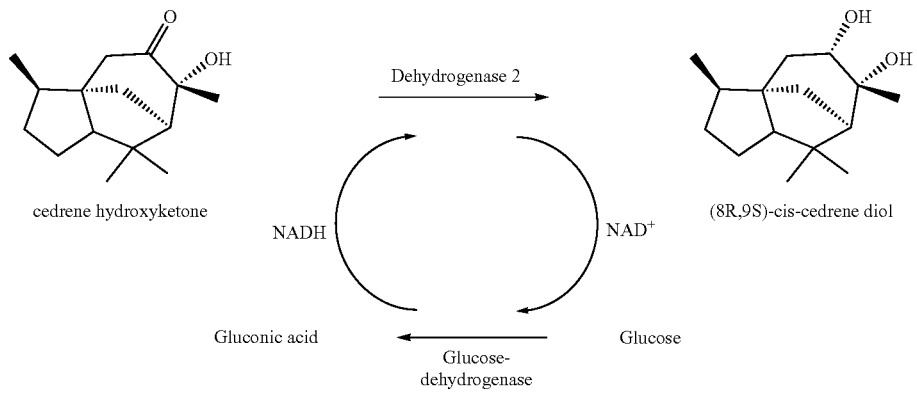

This enzyme oxidizes glucose irreversibly to gluconate using up NAD and forming NADH. The latter is then used by dehydrogenase 2 (Scheme 4). The use of a regeneration system leads to a shift of the equilibrium to the product side due to the excess of the cofactor.

Unfortunately, the regeneration systems are quite expensive and the enzymatic activity is rather low, so that the reactions are slow and the stability of the enzymes may not be sufficient for a longer use. In addition, the high cost of the regeneration systems and the required cosubstrate are a disadvantage.

In the context of the present invention, however, this option in not possible because both, the cofactor NAD and the cofactor NADH are required. An excess of NADH would completely repress the formation of the cedrene hydroxyketone.

cosubstrates are used for the regeneration reaction, which can be easily removed from the system. A prominent example is the alcohol dehydrogenase of *Thermoanaerobacter* brockii, which is capable to provide both, NADH and NADPH by oxidation of the cheap substrate 2-propanol to aceton, and thus supply the desired reaction with the same enzyme (Bogin, O.; Peretz, M.; Burstein, Y. (1997): *Thermoanaerobacter* brockii alcohol dehydrogenase: characterization of the active site metal and its ligand amino acids. Protein Science, 6, 450-458). The desired adjustment of the equilibrium reaction can be achieved by excess of the second substrate here too.

Generally, the enzyme and substrate coupled regeneration proceed similarly. The target reaction is pushed in the desired direction by a second reaction.

Scheme 5: Possible reactions in case of an NADH excess

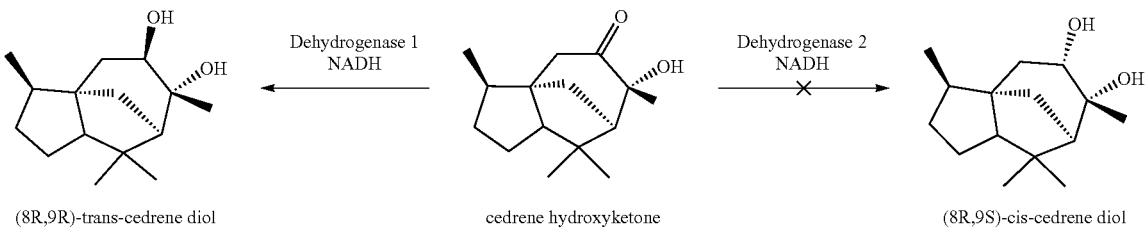

(8R,9R)-trans-cedrene diol      cedrene hydroxyketone      (8R,9S)-cis-cedrene diol Unexpectedly, it is possible to perform both steps using the same enzyme without obtaining an unfavorable equilibrium between cis- and trans-diol. Thus, both steps can be performed in a one pot reaction using only one enzyme.

Therefore, in a preferred embodiment of the method described above, the same enzyme catalyzes the conversion in step (i) and step (ii).

The direct conversion of trans- to cis-diol proceeds without additional (regeneration) enzymes for the regeneration of NAD/NADH and the corresponding cosubstrates. In the direct conversion, a mixture of trans-diol, hydroxyketone and cis-diol is obtained because per oxidized trans-diol only one hydroxyketone can be reduced, i.e. either to a trans- or Scheme 6: Conversion of trans- to cis-cedrene diol by a dehydrogenase with cofactor re-generation

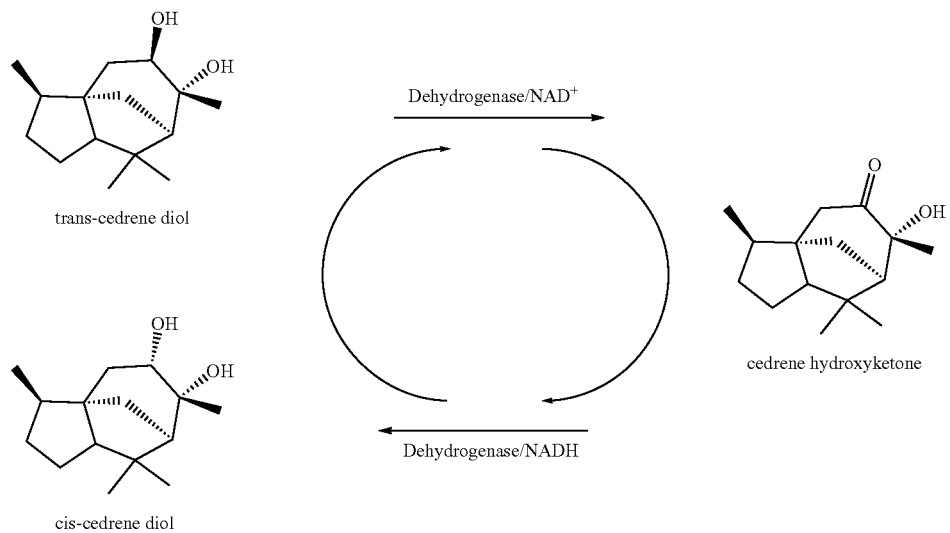

In this so-called substrate coupled cofactor regeneration, no second enzyme is needed, because the enzyme, which catalyzes the desired reaction, also performs the regeneration reaction. According to the prior art, mostly cheaper a cis-diol. However, the cis-diol is barely reoxidated, so that over time cis-diol is accumulated. While this auto-catalytic process leads to a mixture of products, it does not require expensive regeneration enzymes or cosubstrates.

In one embodiment of the method described above, a cofactor is used for the reaction of the enzyme and wherein the cofactor is selected from the group consisting of NAD, NADP, FAD and PQQ.

Preferably, the cofactor is regenerated by an enzymatic regeneration system or the enzyme is the same in step (i) and step (ii) and the cofactor is regenerated by the enzyme.

Surprisingly, it was found out in the context of the present invention, that the 3-alpha-hydroxysteroid dehydrogenase from *Comamonas testosteroni* is capable to oxidize both, trans-cedrene diol and also cis-cedrene diol to cedrene hydroxyketone.

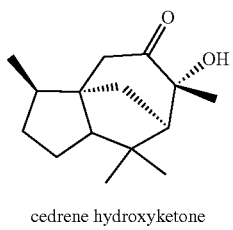

cedrene hydroxyketone

Scheme 7: Reactions of hydroxysteroid dehydrogenase with cedrene hydroxyketone

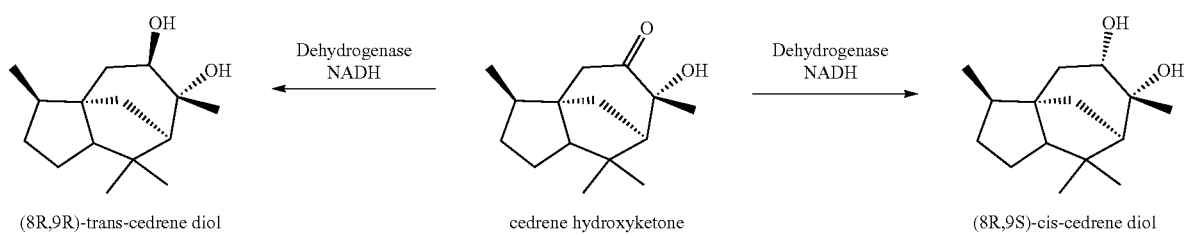

(8R,9R)-trans-cedrene diol     cedrene hydroxyketone     (8R,9S)-cis-cedrene diol Depending on the reaction conditions, cedrene hydroxyketone can be obtained in high yield and high purity. Thus, cis- and trans-cedrene diols can be completely oxidized to the desired cedrene hydroxyketone using up NADH. A regeneration system can be used for NAD in order to push the reaction in the desired direction. It is also possible, however, to use the oxidation of NADH, which naturally occurs in raw extracts. In case of a low dehydrogenase activity in raw extracts with respect to the amount of trans-diol as substrate, the formation of cis-diol from trans-diol is favored. When the regeneration of NAD can only proceed by reduction of hydroxyketone to diol, cis-diol is accumulated. The oxidation, which naturally occurs in raw extracts is catalyzed by the activity of unidentified enzymes, which are present in the raw extract. If the naturally occurring oxidation in the raw extract is high, less trans- and cis-diols are formed. The activity can be adjusted within certain limits by the preparation of the raw extract. For example, a high temperature decreases the activity, presumably by denaturation.

In case cedrene hydroxyketone is used as substrate for the synthesis of cedrene diols, it can be reduced by an excess of NADH. Several options of product formation are possible in this case. If the reaction is not stereo selective, an isomer mixture of 50% cis- and 50% trans-cedrene diol is obtained.

If the reaction is stereo selective, however, depending on how high the stereo selectivity is, either a mixture of cis- and trans-diol or, ideally, only one of the two isomers is obtained. This in usually desirable, because commonly only one of the two isomers has the desired properties. Exactly this surprising feature is exhibited by the 3-alpha-hydroxysteroid dehydrogenase from *Comamonas testosteroni* with cedrene hydroxyketone. In the reduction, the (8R,9S)-cis-cedrene diol is formed practically exclusively (Scheme 9).

Scheme 9: Stereo selective reduction of cedrene hydroxyketone with a hydroxysteroid de-hydrogenase to (8R,9S)-cis-cedrene diol.

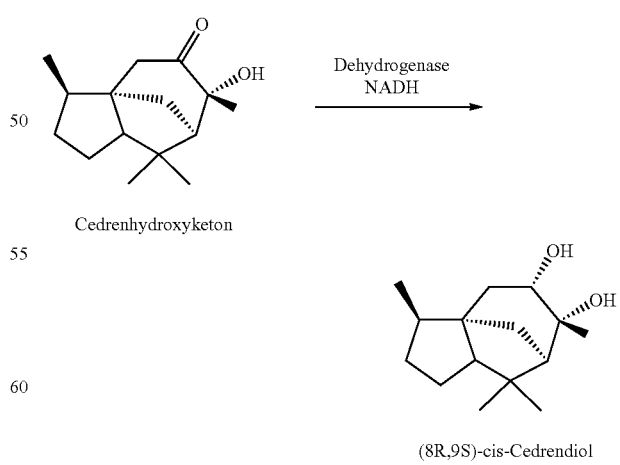

Cedrenhydroxyketon (8R,9S)-cis-Cedrendiol

Scheme 8: Oxidation of (8R,9S)-cis-cedrene diol using a hydroxysteroid dehydrogenase

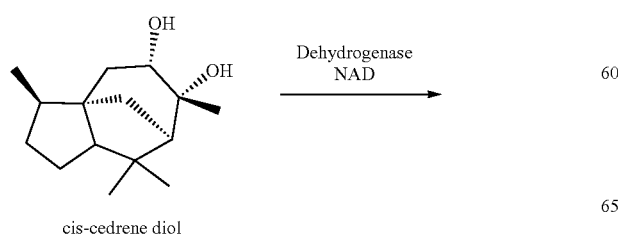

cis-cedrene diol

The 3-alpha-hydroxysteroid dehydrogenase from *Comamonas testosteroni* has been isolated and characterized (Oppermann, U. C. T; Maser, E. (1996): Characterization of a 3a-hydroxysteroid dehydrogenase/carbonyl reductase from the gram-negative bacterium *Comamonas testosteroni*. Eur. J. Biochem., 241, 744-749; Maser, E.; Moebus, E.; Xiong, G. (2000): Functional expression, purification, and characterization of 3α-hydroxysteroid dehydrogenase/carbonyl reductase from *Comamonas testosteroni*, Biochem. Biophys. Research Comm., 272, 622-628). In addition, the gene sequence has been published (Moebus, E; Maser, E. (1998): Molecular cloning, overexpression, and characterization of steroid-inducible 3α-hydroxysteroid dehydrogenase/carbonyl reductase from *Comamonas testosteroni*, J. Biol. Chem., 273 (47), 30888-30896).

Using different steroids as substrates, it was demonstrated, that the enzyme has a high stereo selectivity towards its substrates (Oppermann, U. C. T; Maser, E. (1996): Characterization of a 3α-hydroxysteroid dehydrogenase/ carbonyl reductase from the gram-negative bacterium *Comamonas testosteroni*. Eur. J. Biochem., 241, 744-749). Other authors report the ability of the enzyme to convert xenobiotics.

Surprisingly, it was found in the context of the present invention that the enzyme can stereoselectively oxidize cedrene diols and reduce cedrene hydroxyketone. Particularly surprising was the observation that cedrene hydroxyketone was reduced to the desired (8R,9S)-cis-cedrene diol with high stereo selectivity.

The present invention also relates to the use of an enzyme, which is encoded by a nucleic acid sequence of SEQ ID NO: 1 or a nucleic acid sequence having at least 80%, at least 85%, at least 90%, at least 91%, at least 92%, at least 93%, at least 94%, at least 95%, at least 96%, at least 97%, at least 98% or at least 99% sequence identity to SEQ ID NO: 1, or wherein the enzyme comprises an amino acid sequence of SEQ ID NO: 2 or an amino acid sequence having at least 80%, at least 85%, at least 90%, at least 91%, at least 92%, at least 93%, at least 94%, at least 95%, at least 96%, at least 97%, at least 98% or at least 99% sequence identity to SEQ ID NO: 2 for the conversion of a trans-diol to a cis-diol or for the conversion of a trans-diol or a cis-diol to a hydroxyketone and/or the conversion of a hydroxyketone to a trans-diol or a cis-diol.

Preferably, in the use described above, the two hydroxyl groups of the trans-diol and/or the cis-diol is/are attached to an aliphatic ring system comprising 2 to 4 bridged or non-bridged rings. In this context "attached to an aliphatic ring system" means that the hydroxyl groups occupy two adjacent (vicinal) positions of a ring in the ring system. Preferably, the two hydroxyl groups of the trans-diol and/or the cis-diol is/are attached to a steroid compound.

Preferably, in the enzyme is used in the conversion as described above, wherein the trans-diol is (8R,9R)-trans-cedrene diol and the cis-diol is (8R,9S)-cis-cedrene diol.

Particularly preferably, the enzyme is used in a method as described above.

Example 1: Production of a gene construct for limonene-1,2-epoxide hydrolase Cloning of limonene-1,2-epoxide hydrolase from *Rhodococcus erythropolis* can be performed by standard methods. The limA gene with the entry number Q9ZAG3 (Uniport) is used (GenBank accession code: CAA77012.1). The coding sequence is represented by SEQ ID NO: 3 and the amino acid sequence of the translated protein is represented by SEQ ID NO: 4. Commercially available expression vectors can be used. For example, the pET3a plasmid by Novagen is suitable. It comprises an N-terminal T7 tag and a BamH I restriction site. The Lac operon is used as promotor. The plasmid includes an ampicillin resistance gene as selection marker. Host organisms for the expression can be selected from any state of the art systems. For example, BL21 *Escherichia coli* strains can be used.

As a construct for cloning, a sequence according to SEQ ID NO: 5 can be used, which comprises the added BamHI site GGATCC for cloning into the pet3a vector. Furthermore, the construct comprises the NdeI site CATATG for cloning into the pet3a vector. As stop codon, TAA is used.

Example 2: Transformation of *Escherichia coli* BL21

The transformation is performed according to standard methods, e.g. heat transformation as described by Sambrook and Russel (Sambrook, J.; Russell, R. W. (2001): Molecular cloning: a laboratory manual, 3rd ed. Cold spring harbor laboratory press, cold spring harbor, N.Y.).

Example 3: Production of biomass comprising an inducible limonene-1,2-epoxide hydrolase An auto-induction medium is used (e.g. Studier, Protein Expression and Purification, 41 (2005), 207-234). Composition of the base medium for 100 mL: dissolve 1.0 g tryptone, 0.67 g $Na_2HPO_4 \times 7H_2O$ (25 mM), 0.34 g $KH_2PO_4$ (25 mM), 0.27 g $NH_4Cl$ (50 mM), 0.07 g $Na_2SO_4$ (5 mM), 0.5 g yeast extract in deionized water. The pH is adjusted to 8.8. Subsequently, the medium is sterilized at 121° C. for 20 minutes at 1.013 bar overpressure.

Composition carbohydrate supplement: 100 mL carbohydrate supplement (20fold) comprise: dissolve 10.0 g lactose (0.2%), 2.75 g glucose x $H_2O$ (0.05%), 25.0 g glycerol (0.5%) in deionized water. Autoclave at 121° C. for 20 minutes at 1,013 bar overpressure. 2 mL of the carbohydrate supplement are used for 100 mL auto-induction medium.

Magnesium sulfate solution 1M: dissolve 24.65 g magnesium sulfate in 100 mL deionized water. Autoclave at 121° C. for 20 minutes at 1,013 bar overpressure. 0.2 mL (2 mM) of the magnesium sulfate solution are used for 100 mL auto-induction medium.

Trace mineral solution: 100 mL trace mineral solution (1.000fold) comprise: 50 mM $FeCl_3$, 20 mM $CaCl_2$), 10 mM $MnCl_2$, 10 mM $ZnSO_4$, 2 mM $CoCl_2$, 2 mM $CuCl_2$, 2 mM $NiCl_2$, 2 mM $Na_2MoO_4$, 2 mM $Na_2SeO_3$, 2 mM $H_3BO_3$. Dissolve the metals, except iron chloride, according to the following list separately in ca. 60 mM HCl. Dissolve iron chloride 0.1 M in 50 mL 100 fold diluted concentrated hydrochloric acid.

| 50 ml | 0.1M $FeCl_3$—6H2O | 2.70 g/100 ml |
|---|---|---|
| 2 ml | 1.0M $CaCl_2$—2H2O | 15.8 g/100 ml |
| 1 ml | 1.0M $MnCl_2$—4H2O | 19.8 g/100 ml |
| 1 ml | 1.0M $ZnSO_4$—7H2O | 28.8 g/100 ml |
| 1 ml | 0.2M $CoCl_2$—6H2O | 4.76 g/100 ml |
| 2 ml | 0.1M $CuCl_2$—2H2O | 1.70 g/100 ml |
| 1 ml | 0.2M $NiCl_2$—6H2O | 4.76 g/100 ml |
| 2 ml | 0.1M $Na_2MoO_4$—2H2O | 2.42 g/100 ml |
| 2 ml | 0.1M $Na_2SeO_3$ | 1.73 g/100 ml |
| 2 ml | 0.1M $H_3BO_3$ | 0.62 g/100 ml |

Sterile filtrate with a 0.45 μm membrane filter. 0.02 mL of the trace mineral solution are used for 100 mL auto-induction medium.

Ampicillin solution: dissolve 500 mg sodium ampicillin in 10 mL deionized water. Sterile filtrate with a 0.45 μm membrane filter. 0.2 mL of the ampicillin solution are used for 100 mL auto-induction medium (100 μg/mL).

An *Escherichia coli* BL21 strain is used, which carries a IPTG or lactose inducible gene of a epoxide hydrolase on a pet3a-Plasmid. An inoculation loop of *Escherichia coli* BL21 of a well grown dYT agar plate (24 hours at 30° C.) is used for inoculation of 100 mL auto-induction medium with 100 μg ampicillin in a 500 mL Erlenmeyer flask with baffle. The cultivation is performed at 30° C. and 120 U/min for 18 hours. Typically, the optical density is at 6-9 (600 nm) at this point. Composition of the dYT medium: 5 g/L NaCl; 16.0 g/L tryptone; 10.0 g yeast extract. The pH is adjusted to 7. Autoclave at 121° C. for 20 minutes at 1,013 bar overpressure.

Example 4: Biotransformation with a limonene-1,2-epoxide hydrolase containing biomass The culture broth of example 3 is used. 100 mg (-)-α-cedrene epoxid are added to 100 mL culture broth. Biotransformation is performed at 30° C. and 120 U/min. Optionally, cell membrane damaging agents such as Triton™ X-100 (t-Octylphenoxypolyethoxyethanol), EDTA or organic solvents can be added, which accelerate uptake of the epoxide. The conversion is monitored by gas chromatography. After 96 hours, the conversion is 33.9% trans-cedrene diol.

Example 5: Production of a limonene-1,2-epoxide hydrolase containing raw extract The culture broth of example 3 is used. The culture broth is centrifuged at 4.000 g for 5 minutes in falcon tubes. The supernatant is discarded and the biomass is resuspended in 10 mL 50 mM phosphate buffer (pH 7). Subsequently, the cell disruption is performed by sonification in a falcon tube with a Bandelin Sonoplus UW2200 Sonifier 1×5 minutes, 40% performance, cycle 1 in an ice bath. The raw extract is centrifuged at 12.500 g for 10 minutes at 5° C. The epoxide hydrolase containing supernatant is removed and stored in an ice bath. The residue is discarded.

Example 6: Biotransformation with limonene-1,2-epoxide hydrolase containing raw extract The culture broth of example 3 is used. 100 μL (-)-α-cedrene epoxide are added to the culture broth. The biotransformation is performed at 30° C. and 120 U/min in a 500 mL Erlenmeyer flask with baffle. The conversion is monitored by gas chromatography. After 96 hours, the conversion is 62.9% trans-(8R,9R)-cedrene diol. Other products are not present.

Example 7: Biotransformation with resting cells, which have expressed a limonene-1,2-epoxide hydrolase The culture broth of example 3 is centrifuged at 4.000 g for 5 minutes in falcon tubes. The supernatant is discarded and the biomass is resuspended is 100 mL 50 mM phosphate buffer (pH 7). The cultivation is performed at 30° C. and 120 U/min. After 8 hours, 100 μL (-)-α-cedrene epoxide and 10 mg Triton™ X-100 (t-Octylphenoxypolyethoxyethanol) are added to the resting cells. Optionally, membrane damaging agents such as EDTA or organic solvents can be added. The biotransformation is performed at 30° C. and 120 U/min. The conversion is monitored by gas chromatography. After 72 hours, the conversion is 27.5% trans-(8R,9R)-cedrene diol. Other products are not present.

Example 8: Production of a hydroxysteroid dehydrogenase gene construct

Cloning of hydroxysteroid dehydrogenase from *C. testosteroni* can be performed by standard methods. The hsdA gene with the entry number P80702 (Uniport) is used. The coding sequence is represented by SEQ ID NO: 1 and the amino acid sequence of the translated protein is represented by SEQ ID NO: 2. Commercially available expression vectors can be used. For example, the pet3a plasmid by Novagen is suitable. It comprises an N-terminal T7 tag and a BamH I restriction site. The Lac operon is used as promotor. The plasmid includes an ampicillin resistance gene as selection marker. Host organisms for the expression can be selected from any state of the art systems. For example, BL21 *Escherichia coli* strains can be used.

As a construct for cloning, a sequence according to SEQ ID NO: 6 can be used, which additionally comprises the BamHI site GGATCC for cloning into the pet3a vector. In addition, the construct comprises the NdeI site CATATG for cloning into the pet3a vector. As stop codon, TGA is used.

Example 9: Transformation of *Escherichia coli* BL21

The transformation is preformed according to standard methods, e.g. heat transformation as described by Sambrook and Russel (Sambrook, J.; Russell, R. W. (2001): Molecular cloning: a laboratory manual, 3rd ed. Cold spring harbor laboratory press, cold spring harbor, N.Y.).

Example 10: Production of a biomass with an inducible hydroxyl steroid dehydrogenase An auto-induction medium is used (e.g. Studier, Protein Expression and Purification, 41 (2005), 207-234). Composition of the base medium for 100 mL: dissolve 1.0 g tryptone, 0.67 g $Na_2HPO_4 \times 7H_2O$ (25 mM), 0.34 g $KH_2PO_4$ (25 mM), 0.27 g $NH_4Cl$ (50 mM), 0.07 g $Na_2SO_4$ (5 mM), 0.5 g yeast extract in deionized water. The pH is adjusted to 8.8. Subsequently, the medium is sterilized at 121° C. for 20 minutes at 1.013 bar overpressure.

Composition carbohydrate supplement: 100 mL carbohydrate supplement (20fold) comprise: dissolve 10.0 g lactose (0.2%), 2.75 g glucose x $H_2O$ (0.05%), 25.0 g glycerol (0.5%) in deionized water. Autoclave at 121° C. for 20 minutes at 1,013 bar overpressure. 2 mL of the carbohydrate supplement are used for 100 mL auto-induction medium.

Magnesium sulfate solution 1M: dissolve 24.65 g magnesium sulfate in 100 ml deionized water. Autoclave at 121° C. for 20 minutes at 1,013 bar overpressure. 0.2 mL (2 mM) of the magnesium sulfate solution are used for 100 mL auto-induction medium.

Trace mineral solution: 100 mL trace mineral solution (1.000fold) comprise: 50 mM $FeCl_3$, mM $CaCl_2$), 10 mM $MnCl_2$, 10 mM $ZnSO_4$, 2 mM $CoCl_2$, 2 mM $CuCl_2$, 2 mM $NiCl_2$, 2 mM $Na_2MoO_4$, 2 mM $Na_2SeO_3$, 2 mM $H_3BO_3$. Dissolve the metals, except iron chloride, according to the following list separately in ca. 60 mM HCl. Dissolve iron chloride 0.1 M in 50 mL 100fold diluted concentrated hydrochloric acid.

| | | |
|---|---|---|
| 50 ml | 0.1M FeCl₃—6H2O | 2.70 g/100 ml |
| 2 ml | 1.0M CaCl₂—2H2O | 15.8 g/100 ml |
| 1 ml | 1.0M MnCl₂—4H2O | 19.8 g/100 ml |
| 1 ml | 1.0M ZnSO₄—7H2O | 28.8 g/100 ml |
| 1 ml | 0.2M CoCl₂—6H2O | 4.76 g/100 ml |
| 2 ml | 0.1M CuCl₂—2H2O | 1.70 g/100 ml |
| 1 ml | 0.2M NiCl₂—6H2O | 4.76 g/100 ml |
| 2 ml | 0.1M Na₂MoO₄—2H2O | 2.42 g/100 ml |
| 2 ml | 0.1M Na₂SeO₃ | 1.73 g/100 ml |
| 2 ml | 0.1M H₃BO₃ | 0.62 g/100 ml |

Sterile filtrate with a 0.45 µm membrane filter. 0.02 mL of the trace mineral solution are used for 100 mL auto-induction medium.

Ampicillin solution: dissolve 500 mg sodium ampicillin in 10 mL deionized water. Sterile filtrate with a 0.45 µm membrane filter. 0.2 mL of the ampicillin solution are used for 100 mL auto-induction medium (100 µg/mL).

An *Escherichia coli* BL21 strain is used, which carries a IPTG or lactose inducible gene of a 3-a-hydroxysteroid dehydrogenase on a pet3a-Plasmid. An inoculation loop of *Escherichia coli* BL21 of a well grown dYT agar plate (24 hours at 30° C.) is used for inoculation of 100 mL auto-induction medium with 100 µg ampicillin in a 500 mL Erlenmeyer flask with baffle. The cultivation is performed at 30° C. and 120 U/min for 18 hours. Typically, the optical density is at 6-9 (600 nm) at this point. Composition of the dYT medium: 5 g/L NaCl; 16.0 g/L tryptone; 10.0 g yeast extract. The pH is adjusted to 7. Autoclave at 121° C. for 20 minutes at 1,013 bar overpressure.

Example 11: Biotransformation with a hydroxysteroid dehydrogenase containing biomass The culture broth of example 10 is used. 50 mg trans-cedrene diol are added to 100 ml culture broth. Biotransformation is performed at 30° C. and 120 U/min. Optionally, cell wall or membrane damaging agents such as Triton™ X-100 (t-Octylphenoxypolyethoxy-ethanol), EDTA, lysozym or organic solvents can be added, which accelerate substrate uptake. The conversion is monitored by gas chromatography. After 24 hours, the conversion is 45% cedrene hydroxyketone.

Example 12: Production of a hydroxysteroid dehydrogenase containing raw extract The culture broth of example 10 is used. The culture broth is centrifuged at 4.000 g for 5 minutes in falcon tubes. The supernatant is discarded and the biomass is resuspended in 10 mL 200 mM phosphate buffer (pH 8). Subsequently, the cell disruption is performed by sonification in a falcon tube with a Bandelin Sonoplus UW2200 Sonifier 1×5 minutes, 40% performance, cycle 1 in an ice bath. The raw extract is centrifuged at 12.500 g for 10 minutes at 5° C. The dehydrogenase containing supernatant is removed and stored in and ice bath. The residue is discarded.

The culture broth can be concentrated by methods known to the skilled person, such as e.g. membrane filtration, precipitation with salts (e.g. ammonium sulfate) or crystallization. It is also possible to use chromatographic methods for concentration of the 3-α-hydroxysteroid dehydrogenase. A good purification method is affinity chromatography. In this method, a modified 3-α-hydroxysteroid dehydrogenase is used, which carries a 6-histidine residue at the N-terminus. This is achieved on genetic level by a corresponding extension of the 3-α-hydroxysteroid dehydrogenase gene.

Example 13: Synthesis of cedrene hydroxyketone from (8R,9R)-trans-cedrene diol with a hydroxysteroid dehydrogenase containing raw extract A culture broth from example 10 is used. 20 mg trans-cedrene diol, 2 g/L Tween® 80 (Polyethylene glycol sorbitan monooleate) and 25 µL ampicilin solution (50 mg/mL) are added to 10 mL culture broth (protein content 18 g/L) in a 50 mL falcon tube with a magnetic stir bar. The biotransformation is performed at 30° C., but it can be higher or lower. The conversion is monitored by gas chromatography. After 21 hours, the conversion is 76.1% cedrene hydroxyketone. No other products are present.

Example 14: Stereo selective reduction of cedrene hydroxyketone to a (8R,9S)-cis-cedrene diol A culture broth from example 10 is used. The biotransformation is performed at 30° C., but it can be higher or lower. 200 mg cedrene hydroxyketone, 2 g/L Tween® 80 (Polyethylene glycol sorbitan monooleate), 10 mg protease inhibitor 8830 (Sigma Aldrich) and 100 µL ampicillin solution (50 mg/mL) are added to 120 mL culture broth (protein content 15.9 g/L) in a 250 mL Schott flask with a magnetic stir bar. 20 mg NAD and 3.3 g glucose monohydrate are added to the solution. Subsequently, 4.4 mg commercial glucose dehydrogenase (activity >25U/mg) in 1 mL buffer is added. The conversion proceeds at a constant pH 7 with automatic addition of 1 M lye. After 27.5 and 47.5 hours, another 20 mg NAD are added. After 30.5 hours, an additional 1.5 g glucose monohydrate are added. The conversion is monitored by gas chromatography. After 71.5 hours, the conversion is 84.9% cis-cedrene diol. No other products are present.

Example 15: Direct stereo selective conversion of (8R,9R)-trans-cedrene diol to (8R,9S)-cis-cedrene diol with a hydroxysteroid dehydrogenase containing raw extract A culture broth from example 10 is used. The biotransformation is performed at 40° C., but it can be higher or lower. 500 mg trans-cedrene diol and 500 mg cedrene hydroxyketone, 2 g/L Tween® 80 (Polyethylene glycol sorbitan monooleate), 10 mg protease inhibitor 8830 (Sigma Aldrich) and 100 µL ampicillin solution (50 mg/mL) are added to 50 mL culture broth (protein content 25 g/L) in a 250 mL Schott flask with a magnetic stir bar. 120 mg NAD are added to the solution. After 16 hours, another 500 mg trans-cedrene diol are added. After 66 hours, an additional 60 mg NAD are added. The conversion is monitored by gas chromatography. After 95.5 hours, the trans-cedrene diol is entirely converted. The product mixture comprises 29.9% cis-cedrene diol and 70.1% cedrene hydroxyketone.

Sequences:
SEQ ID NO: 1: coding region of the hedA gene from *Comamonas testosteroni*
SEQ ID NO: 2: translated sequence of hedA gone from *Comamonas testosteroni*
SEQ ID NO: 3: coding region of the limA gone from *Rhodococcus erythropolis*
SEQ ID NO: 4: translated sequence of limA gene from *Rhodococcus erythropolis*
SEQ ID NO: 5: construct of limA for cloning into pet3a vector used in example 1

SEQ ID NO: 6 construct of hedA for cloning into pet3a vector used in example 8

The invention claimed is:

1. A method for the production of a trans-diol or a cis-diol or a hydroxyketone comprising the step(s)

(i) conversion of a trans-diol or a cis-diol to a hydroxyketone catalyzed by an enzyme, which is encoded by a nucleic acid sequence of SEQ ID NO: 1 or a nucleic acid sequence having at least 90% sequence identity to SEQ ID NO: 1, or wherein the enzyme comprises the amino acid sequence of SEQ ID NO: 2, or an amino acid sequence having at least 90% sequence identity to SEQ ID NO: 2, and/or (ii) conversion of a hydroxyketone to a trans diol or a cis-diol catalyzed by an enzyme as defined in step (i); and wherein the two hydroxyl groups of the trans-diol and/or the cis-diol is/are attached to an aliphatic ring system comprising 2 to 4 bridged or non-bridged rings;

wherein the trans-diol is (8R,9R)-trans-cedrene diol, the cis-diol is (8R,9S)-cis-cedrene diol and the hydroxyketone is cedrene hydroxyketone.

2. The method of claim 1 for the production of a cis-diol comprising the step(s)
   (i) conversion of a trans-diol to a hydroxyketone catalyzed by an enzyme, which is encoded by a nucleic acid sequence of SEQ ID NO: 1 or a nucleic acid sequence having at least 90% sequence identity to SEQ ID NO: 1, or wherein the enzyme comprises an amino acid sequence of SEQ ID NO: 2 or an amino acid sequence having at least 90% sequence identity to SEQ ID NO: 2, and
   (ii) conversion of a hydroxyketone, optionally the hydroxyketone obtained in step (i), to a cis-diol catalyzed by an enzyme as defined in step (i).

3. The method of claim 1 for the production of (8R,9S)-cis-cedrene diol, wherein in step (i) (8R,9R)-trans-cedrene diol is converted to cedrene hydroxyketone and in step (ii) cedrene hydroxyketone is converted to (8R,9S)-cis-cedrene diol.

4. The method of claim 1, wherein the same enzyme catalyzes the conversion in step (i) and step (ii).

5. The method of claim 1, wherein a cofactor is used for the reaction of the enzyme and wherein the cofactor is selected from the group consisting of NAD, NADP, FAD and PQQ.

6. The method of claim 5, wherein the cofactor is regenerated by an enzymatic regeneration system or wherein the enzyme is the same in step (i) and step (ii) and the cofactor is regenerated by the enzyme.

\* \* \* \* \*

```
                        SEQUENCE LISTING

<160> NUMBER OF SEQ ID NOS: 6

<210> SEQ ID NO 1
<211> LENGTH: 771
<212> TYPE: DNA
<213> ORGANISM: Comamonas testosteroni

<400> SEQUENCE: 1
atgtccatca tcgtgataag cggctgcgcc accggcattg gtgcggctac gcgcaaggtc      60
ctggaggcgg ccggtcacca gatcgtaggc atcgatatac gcgatgcgga agtgattgcc     120
gatctctcga cggccgaagg tcgaaagcag gcgattgccg atgtactggg aagtgcagc      180 aagggcatgg acggcctggt gctgtgcgcc ggcctgggac cgcagaccaa ggtgcttggc     240
aatgtggttt cggtcaatta tttttggcgcg accgagctga tggatgcctt tttgccagcg    300
ctgaaaaaag gccatcagcc cgcagccgtc gtcatctcgt ccgtggcttc cgcgcatctg     360
gcttttgaca agaacccact ggcgctggca ctggaagccg gcgaggaagc caaggcccgc     420
gccattgtcg aacatgcggg agagcagggc ggaaatctgg cctatgcggg cagcaagaat     480
gctttgacgg tggctgtgcg caaacgcgcc gccgctgggg gcgaggctgg cgtgcgcctg     540
aacaccatcg ccccggtgc aaccgagact cccttgctgc aggcgggcct gcaggacccg      600
cgctatggcg aatccattgc caagttcgtt cctcccatgg gccgccgtgc cgagccgtcc     660
gagatggcgt cggtcatcgc cttttttgatg agcccggccg caagctatgt gcatggcgcg    720
cagatcgtca ttgatggcgg cattgatgcg gtgatgcgcc cgacacagtt c              771

<210> SEQ ID NO 2
<211> LENGTH: 257
<212> TYPE: PRT
<213> ORGANISM: Comamonas testosteroni

<400> SEQUENCE: 2

Met Ser Ile Ile Val Ile Ser Gly Cys Ala Thr Gly Ile Gly Ala Ala
1               5                   10                  15

Thr Arg Lys Val Leu Glu Ala Ala Gly His Gln Ile Val Gly Ile Asp
                20                  25                  30

Ile Arg Asp Ala Glu Val Ile Ala Asp Leu Ser Thr Ala Glu Gly Arg
            35                  40                  45

Lys Gln Ala Ile Ala Asp Val Leu Ala Lys Cys Ser Lys Gly Met Asp
        50                  55                  60

Gly Leu Val Leu Cys Ala Gly Leu Gly Pro Gln Thr Lys Val Leu Gly
65                  70                  75                  80

Asn Val Val Ser Val Asn Tyr Phe Gly Ala Thr Glu Leu Met Asp Ala
                85                  90                  95

Phe Leu Pro Ala Leu Lys Lys Gly His Gln Pro Ala Ala Val Val Ile
                100                 105                 110

Ser Ser Val Ala Ser Ala His Leu Ala Phe Asp Lys Asn Pro Leu Ala
            115                 120                 125

Leu Ala Leu Glu Ala Gly Glu Glu Ala Lys Ala Arg Ala Ile Val Glu
        130                 135                 140

His Ala Gly Glu Gln Gly Gly Asn Leu Ala Tyr Ala Gly Ser Lys Asn
145                 150                 155                 160

Ala Leu Thr Val Ala Val Arg Lys Arg Ala Ala Ala Trp Gly Glu Ala
                165                 170                 175
```

Gly Val Arg Leu Asn Thr Ile Ala Pro Gly Ala Thr Glu Thr Pro Leu
            180                 185                 190

Leu Gln Ala Gly Leu Gln Asp Pro Arg Tyr Gly Glu Ser Ile Ala Lys
        195                 200                 205

Phe Val Pro Pro Met Gly Arg Arg Ala Glu Pro Ser Glu Met Ala Ser
    210                 215                 220

Val Ile Ala Phe Leu Met Ser Pro Ala Ala Ser Tyr Val His Gly Ala
225                 230                 235                 240

Gln Ile Val Ile Asp Gly Gly Ile Asp Ala Val Met Arg Pro Thr Gln
                245                 250                 255

Phe

<210> SEQ ID NO 3
<211> LENGTH: 447
<212> TYPE: DNA
<213> ORGANISM: Rhodococcus erythropolis

<400> SEQUENCE: 3
atgacatcaa agatcgaaca acctcgctgg gcgtccaagg acagtgccgc cggcgctgcc        60
tcgactccgg acgaaaagat cgttctggag ttcatggacg cactgaccag taatgatgct       120
gcaaaactca ttgagtactt tgcagaagac acgatgtacc agaacatgcc actccccct        180 gcatacggcc gcgacgccgt cgagcaaact ctggctggcc tgttcaccgt catgagcatc       240
gatgcggtgg agacgttcca tatcggctcg agtaacggac ttgtgtacac cgaacgtgtc       300
gatgtcctac gcgcactacc caccggcaag agctacaacc tgtcaatcct cggagtcttc       360
cagctcaccg agggcaagat tacgggttgg cgtgactact tcgatctgcg cgaattcgaa       420
gaagctgtcg accttcccct ccgcggc                                           447

<210> SEQ ID NO 4
<211> LENGTH: 149
<212> TYPE: PRT
<213> ORGANISM: Rhodococcus erythropolis

<400> SEQUENCE: 4

Met Thr Ser Lys Ile Glu Gln Pro Arg Trp Ala Ser Lys Asp Ser Ala
1               5                   10                  15

Ala Gly Ala Ala Ser Thr Pro Asp Glu Lys Ile Val Leu Glu Phe Met
            20                  25                  30

Asp Ala Leu Thr Ser Asn Asp Ala Ala Lys Leu Ile Glu Tyr Phe Ala
        35                  40                  45

Glu Asp Thr Met Tyr Gln Asn Met Pro Leu Pro Pro Ala Tyr Gly Arg
    50                  55                  60

Asp Ala Val Glu Gln Thr Leu Ala Gly Leu Phe Thr Val Met Ser Ile
65                  70                  75                  80

Asp Ala Val Glu Thr Phe His Ile Gly Ser Ser Asn Gly Leu Val Tyr
                85                  90                  95

Thr Glu Arg Val Asp Val Leu Arg Ala Leu Pro Thr Gly Lys Ser Tyr
            100                 105                 110

Asn Leu Ser Ile Leu Gly Val Phe Gln Leu Thr Glu Gly Lys Ile Thr
        115                 120                 125

Gly Trp Arg Asp Tyr Phe Asp Leu Arg Glu Phe Glu Glu Ala Val Asp
    130                 135                 140

Leu Pro Leu Arg Gly
145

```
<210> SEQ ID NO 5
<211> LENGTH: 459
<212> TYPE: DNA
<213> ORGANISM: Artificial Sequence
<220> FEATURE:
<223> OTHER INFORMATION: synthetic construct

<400> SEQUENCE: 5
catatgacat caaagatcga acaacctcgc tgggcgtcca aggacagtgc cgccggcgct      60
gcctcgactc cggacgaaaa gatcgttctg gagttcatgg acgcactgac cagtaatgat     120
gctgcaaaac tcattgagta ctttgcagaa gacacgatgt accagaacat gccactcccc     180
cctgcatacg gccgcgacgc cgtcgagcaa actctggctg gcctgttcac cgtcatgagc     240
atcgatgcgg tggagacgtt ccatatcggc tcgagtaacg gacttgtgta caccgaacgt     300
gtcgatgtcc tacgcgcact acccaccggc aagagctaca acctgtcaat cctcggagtc     360
ttccagctca ccgagggcaa gattacgggt tggcgtgact acttcgatct gcgcgaattc     420
gaagaagctg tcgaccttcc cctccgcggc taaggatcc                            459

<210> SEQ ID NO 6
<211> LENGTH: 783
<212> TYPE: DNA
<213> ORGANISM: Artificial Sequence
<220> FEATURE:
<223> OTHER INFORMATION: synthetic construct

<400> SEQUENCE: 6
catatgtcca tcatcgtgat aagcggctgc gccaccggca ttggtgcggc tacgcgcaag      60
gtcctggagg cggccggtca ccagatcgta ggcatcgata tacgcgatgc ggaagtgatt     120
gccgatctct cgacggccga aggtcgaaag caggcgattg ccgatgtact ggcgaagtgc     180
agcaagggca tggacggcct ggtgctgtgc gccggcctgg accgcagac caaggtgctt      240 ggcaatgtgg tttcggtcaa ttattttggc gcgaccgagc tgatggatgc cttttttgcca    300 gcgctgaaaa aaggccatca gcccgcagcc gtcgtcatct cgtccgtggc ttccgcgcat     360
ctggcttttg acaagaaccc actggcgctg gcactggaag ccggcgagga agccaaggcc     420
cgcgccattg tcgaacatgc gggagagcag ggcggaaatc tggcctatgc gggcagcaag     480
aatgctttga cggtggctgt gcgcaaacgc gccgccgcct ggggcgaggc tggcgtgcgc     540
ctgaacacca tcgcccccgg tgcaaccgag actcccttgc tgcaggcggg cctgcaggac     600
ccgcgctatg gcgaatccat tgccaagttc gttcctccca tgggccgccg tgccgagccg     660
tccgagatgg cgtcggtcat cgccttttt g atgagcccgg ccgcaagcta tgtgcatggc     720
gcgcagatcg tcattgatgg cggcattgat gcggtgatgc gcccgacaca gttctgagga    780
tcc                                                                    783
```